United States Patent
Adamczyk et al.

(10) Patent No.: US 10,575,969 B2
(45) Date of Patent: Mar. 3, 2020

(54) PROSTHETIC APPARATUS AND METHOD THEREFOR

(71) Applicant: Wisconsin Alumni Research Foundation, Madison, WI (US)

(72) Inventors: Peter Gabriel Adamczyk, Madison, WI (US); Luke J. Steinbach, Madison, WI (US); Michael E. Hahn, Eugene, OR (US)

(73) Assignee: Wisconsin Alumni Research Foundation, Madison, WI (US)

( * ) Notice: Subject to any disclaimer, the term of this patent is extended or adjusted under 35 U.S.C. 154(b) by 9 days.

(21) Appl. No.: 15/671,683

(22) Filed: Aug. 8, 2017

(65) Prior Publication Data

US 2019/0046335 A1 Feb. 14, 2019

(51) Int. Cl.
*A61F 2/66* (2006.01)
*A61F 2/70* (2006.01)
(Continued)

(52) U.S. Cl.
CPC ............... *A61F 2/66* (2013.01); *A61F 2/68* (2013.01); *A61F 2/70* (2013.01); *A61F 2/72* (2013.01); *A61F 2002/502* (2013.01); *A61F 2002/503* (2013.01); *A61F 2002/5018* (2013.01); *A61F 2002/5021* (2013.01); *A61F 2002/5023* (2013.01); *A61F 2002/5027* (2013.01); *A61F 2002/5033* (2013.01); *A61F 2002/5036* (2013.01); *A61F 2002/5043* (2013.01); *A61F 2002/5079* (2013.01); *A61F 2002/6614* (2013.01); *A61F 2002/6642* (2013.01); *A61F 2002/6657* (2013.01); *A61F 2002/6664* (2013.01); *A61F 2002/6671* (2013.01); *A61F 2002/6854* (2013.01); *A61F 2002/701* (2013.01); *A61F 2002/704* (2013.01); *A61F 2002/705* (2013.01); *A61F 2002/741* (2013.01); *A61F 2002/745* (2013.01); *A61F 2002/764* (2013.01); *A61F 2002/7615* (2013.01);
(Continued)

(58) Field of Classification Search
CPC ............................ A61F 2002/6614–2002/6692
USPC ...................................................... 623/53–56
See application file for complete search history.

(56) References Cited

U.S. PATENT DOCUMENTS 5,571,210 A * 11/1996 Lindh ..................... A61F 2/66
                                                                     623/38
9,649,207 B2    5/2017  Hahn et al.
(Continued)

*Primary Examiner* — David H Willse
(74) *Attorney, Agent, or Firm* — Crawford Maunu PLLC

(57) ABSTRACT

Various aspects of the present disclosure characterize apparatuses and/or methods as may be implemented with a variety of prosthetic components and applications. As may be consistent with one or more embodiments described herein, movement parameters pertaining to movement of a user of a prosthetic foot are sensed as the user travels along a surface, with the prosthetic foot having a front ball region and a rear heel region for respectively contacting the surface. A state of movement of the user, including a speed at which the user is travelling along the surface, is determined based on the sensed movement parameters. Utilizing a mechanical actuator, the prosthetic foot is dynamically positioned in response to the speed at which the user is travelling along the surface, by manipulating the mechanical actuator to move the rear heel region relative to the front ball region based on changes in the speed.

20 Claims, 17 Drawing Sheets

(51) Int. Cl.
*A61F 2/68* (2006.01)
*A61F 2/76* (2006.01)
*A61F 2/50* (2006.01)
*A61F 2/72* (2006.01)
*A61F 2/74* (2006.01)

(52) U.S. Cl.
CPC ............... *A61F 2002/7625* (2013.01); *A61F 2002/7635* (2013.01); *A61F 2002/7655* (2013.01); *A61F 2002/7685* (2013.01)

(56) References Cited

U.S. PATENT DOCUMENTS

| | | | | |
|---|---|---|---|---|
| 2003/0120183 A1* | 6/2003 | Simmons | ................. | A61F 4/00 600/595 |
| 2007/0061016 A1* | 3/2007 | Kuo | .......................... | A61F 2/66 623/24 |
| 2016/0175119 A1* | 6/2016 | Kramer | .................... | A61F 2/66 623/24 |
| 2017/0348118 A1 | 12/2017 | Adamczyk et al. | | |

* cited by examiner

PROSTHETIC APPARATUS AND METHOD THEREFOR

FIELD

Aspects of various embodiments are directed to manipulation of prostheses.

BACKGROUND

Prostheses can be useful to enhance the life experience of users, such as for those who lose or are born without a portion of a limb. As the operability of such prostheses improves, so does the experience of the user. Accordingly, prostheses have continued to develop over the years to provide enhanced capabilities.

As features are added to prostheses, their complexity also tends to increase. For instance, where mechanical control and actuation are implemented, related componentry can tend to be bulky and require significant power. Further, prostheses can be challenging to implement under varied conditions of movement, which may range from walking to running. For instance, prostheses that are configured specifically for walking may be difficult or impossible to run with, and prostheses that are configured specifically for running may be cumbersome or awkward for walking.

Other issues with prostheses relate to the challenges that users face in using them. For instance, walking, running, and gaits in-between walking and running can involve very different forces, balance, mechanics and other characteristics. The natural foot-ankle behaves differently for tasks such as walking, running, and standing balance. In particular, running exhibits properties that are significantly different than walking.

These and other matters have presented challenges to the use of prostheses, for a variety of applications.

SUMMARY

Various example embodiments are directed to prosthetics components and their implementation, such as prosthetics components for lower limbs.

According to an example embodiment, an apparatus and/or method involves sensing movement parameters pertaining to movement of a user of a prosthetic foot as the user travels along a surface, with the prosthetic foot having a front ball region and a rear heel region for respectively contacting the surface. A state of movement of the user, including a speed at which the user is travelling along the surface, is determined based on the sensed movement parameters. Utilizing a mechanical actuator, the prosthetic foot is dynamically positioned in response to the speed at which the user is travelling along the surface, by manipulating the mechanical actuator to move the rear heel region relative to the front ball region based on changes in the speed. Manipulating the mechanical actuator may include, for example, increasing or decreasing the height of the rear heel region relative to the front ball region, and/or moving the rear heel region toward or away from the front ball region. In certain embodiments, dynamically positioning the prosthetic foot includes positioning the prosthetic foot under conditions in which the prosthetic foot is not under load, and locking the prosthetic foot in position under conditions in which the prosthetic foot contacts the surface.

In accordance with one or more embodiments, an apparatus includes a mechanical actuator, a sensor circuit and a control circuit, that operate to position a prosthetic foot having a front ball region and a rear heel region for respectively contacting a surface along which a user of the prosthetic foot is travelling. The mechanical actuator is configured and arranged to position the prosthetic foot, based on inputs from the control circuit. The sensor circuit senses movement parameters pertaining to movement of the user. The control circuit operates with the sensor circuit to determine a state of movement of the user, including a speed at which the user is travelling along the surface, based on the movement parameters sensed by the sensor circuit. The control circuit dynamically positions the prosthetic foot in response to the speed at which the user is travelling along the surface, by manipulating the mechanical actuator to move the rear heel region relative to the front ball region based on changes in the speed.

In accordance with another embodiment, an apparatus includes a mechanical actuator and a control circuit. The mechanical actuator is configured and arranged to position a prosthetic foot having a front ball region and a rear heel region for respectively contacting a surface along which a user of the prosthetic foot structure is travelling. The control circuit is configured and arranged with the mechanical actuator to determine a state of movement of the user, including a speed at which the user is travelling along the surface, and to move the rear heel region relative to the front ball region based on changes in the speed, by increasing or decreasing the height of the rear heel region relative to the front ball region, and/or moving the rear heel region toward or away from the front ball region.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

Figure 1:
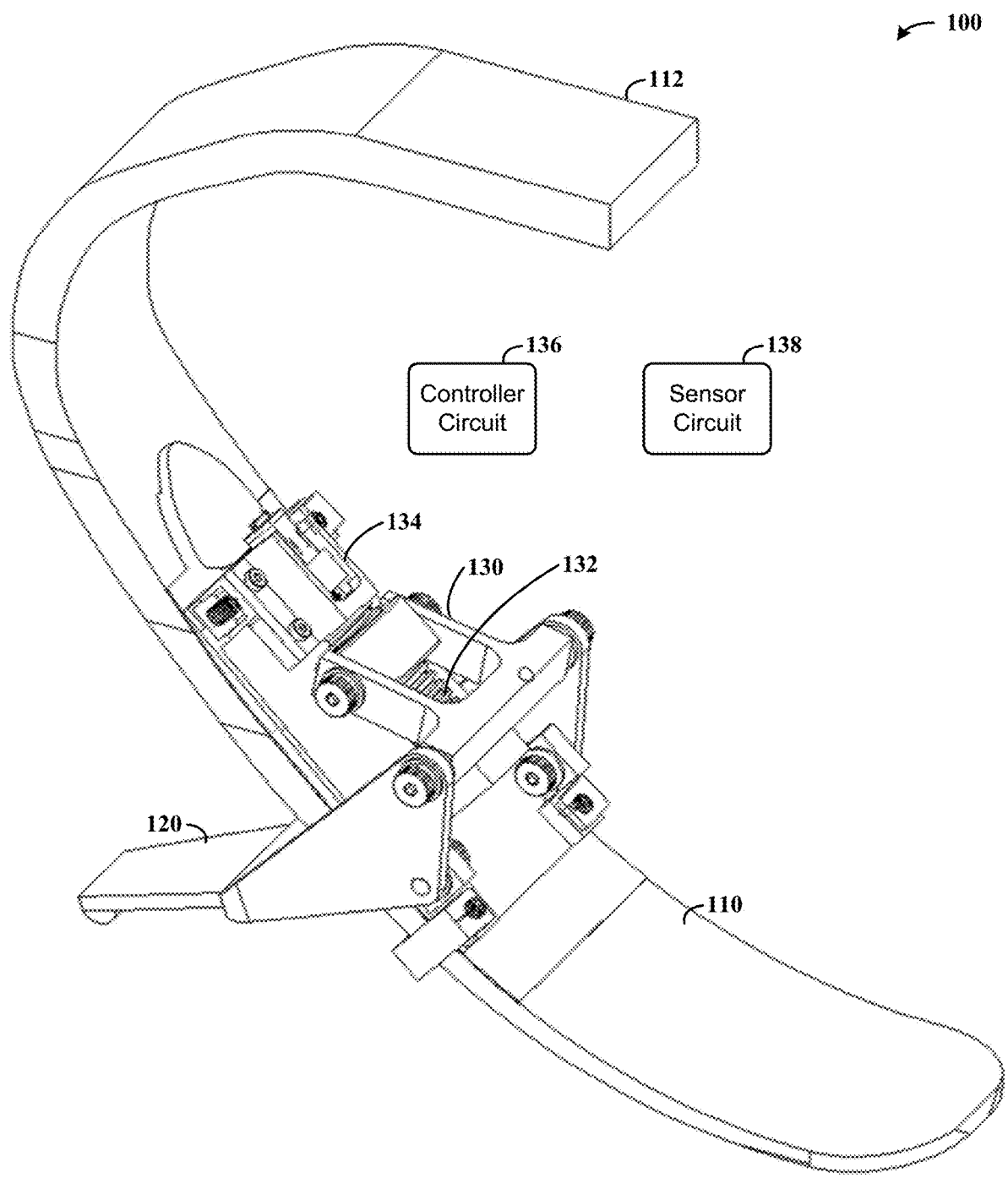
FIG. 1 shows a prosthetic foot apparatus, in accordance with the present invention.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving prostheses, such as those involving the dynamic control of heel elevation or other position in response to increases or decreases in speed of a user of a prosthesis. In certain implementations, aspects of the present disclosure have been shown to be beneficial when used in the context of the positioning of a prosthetic foot for motion ranging from walking to running. Such approaches may involve continually raising the heel relative to the ball of the prosthetic foot as the user's speed increases from a walking pace to a running pace, and correspondingly lowering the heel relative to the ball of the prosthetic foot as the user slows down toward a walking pace. Various approaches address challenges as noted herein, such as those relating to bulky and/or relatively high-power actuators. In this context (and as may relate to one or more embodiments) it has been recognized/discovered that such prosthetic foot manipulation can be carried out while the foot is not loaded, which can allow use of lower-power and/or smaller actuators. While not necessarily so limited, various aspects may be appreciated through a discussion of examples using such exemplary contexts.

Generally, various embodiments are directed to improving the versatility of locomotion with lower limb prostheses, extending across both low-impact walking and higher-impact running tasks. For instance, walking tasks may be implemented with a contact pattern in which the effective ground contact point moves from heel-to-toe during each stance phase, while running tasks may be implemented such that the contact pattern is dominated by the forefoot, particularly as speeds increase. The prosthesis may mimic natural ankle mechanics in walking, and restore natural knee and hip mechanics, or provide running-specific mechanics that facilitate use of a mechanism in which the user keeps his/her knee straight and uses the prosthesis to perform a "bouncing" type motion of running. Accordingly, a single device can be implemented to function in both these modes.

A semi-active actuation may be used to modify properties of the prostheses, such as discussed above, without body-weight scale actuator forces. Actuators adjust the properties of the prosthesis, which continues to be body-powered with respect to leg-ground interaction as related to one or more of force, moment and power. This semi-active approach reduces weight, complexity and cost while still providing desirable operational capabilities with regard to both running-specific activities and walking/standing activities. The prosthesis' properties can be actively modified in order to match multiple tasks with different needs. Accordingly, the versatility of locomotion with lower limb prostheses, extending across both low-impact walking and higher-impact running tasks, can be enhanced.

In particular embodiments, an apparatus operates to suddenly or gradually eliminate a heel member of a prosthetic foot from contributing to ground contact, so the heel end of the foot contributes less or not at all to supporting body weight as speed increases. An actuator and control circuit for the actuator moves a lever system to lift the heel, so that the heel is lifted more at higher speeds, and less at lower speeds.

In some embodiments, a control circuit utilized to control manipulation of a prosthetic foot includes an embedded microcontroller and sensing system, which measure the motion of one or both legs, reconstruct the motion, classify it, and choose and regulate a control action to adjust properties of the prosthetic foot to suit the current task. The measured motion includes raw and processed signals from an inertial motion sensor (acceleration, angular velocity, magnetic field, air pressure (for height)). The processed signals provide a real-time reconstruction of the motion of the foot/prosthesis, and associated estimates of instantaneous velocity, moving-average walking or running speed, and direction of motion. Additional processed signals may include impact detection (as the foot strikes the ground) and pattern recognition.

Measured muscle activity (electromyography (EMG)) may also be used to characterize motion, which is used to manipulate the prosthetic foot as noted above, based on measured muscle activity in one or both legs and/or feet. For general information regarding EMG, and for specific information regarding control methods that may be implemented in accordance with one or more embodiments, reference may be made to U.S. Pat. No. 9,649,207, which is fully incorporated herein by reference. For instance, predictive classification in walking (level vs stairs vs ramps) as noted therein may be leveraged to classify walking states, running states, and transitions between walking and running states.

A variety of prosthetic manipulation approaches can be implemented to suit particular applications. In some embodiments, the forefoot of a prosthetic foot is suddenly or gradually rotated downward (into a "plantarflexed" posture) to promote forefoot-striking running gait. Certain implementations may utilize one or more aspects of the apparatus and approach characterized in U.S. patent application Ser. No. 15/171,519 (Adamczyk, et al.), which is fully incorporated herein by reference. Certain implementations involve suddenly or gradually changing the stiffness of a prosthesis keel to accommodate differences between walking and running and/or differences across walking or running speed. Implementations may also involve suddenly or gradually lengthening the effective length of the leg of the user. Adjusting stiffness may involve utilizing a mechanism that adjusts stiffness by moving a fulcrum supporting a leaf spring keel, to apply increased stiffness relative to the position of the fulcrum.

According to various example embodiments, aspects of the present disclosure are directed to an apparatus and/or implementation thereof, involving one or more manipulators that interact to position a prosthetic foot. Where more than one manipulator is implemented, each manipulator operates relative to the other and, together provide the positioning. In this context, the term manipulator refers to a mechanical component that, when moved relative to another such manipulator or another component, provides positioning, such as to raise or lower a heel region relative to a ball region of a prosthetic foot. In various embodiments, the manipulator includes a drive or other component that generates movement using power, such as provided by a battery. In other embodiments, the manipulator is responsive to a mechanical drive input (e.g., a separate battery/drive component).

As may be implemented in accordance with one or more embodiments, an apparatus includes first and second manipulators that respectively operate to manipulate a prosthetic foot about first and second axes. A sensor circuit senses movement characteristics of the prosthetic foot (e.g., movement, load applied due to movement). The manipulators operate with the sensor circuit to manipulate the prosthetic foot about the first and second axes based on sensed movement characteristics, including speed. The manipulators may further operate to manipulate the prosthetic foot in response to sensed movement characteristics indicating that the prosthetic foot is elevated over a surface. This approach can be implemented, for example, to provide movement of the prosthetic foot while the prosthetic foot is under relatively low/no load, facilitating use of relatively small and/or low-power components for effecting manipulation (e.g., relative to manipulating a prosthetic foot under the load of a user's weight). This approach can further be implemented in a training session to position the prosthetic foot for imbalance training, or in a walking situation in which the foot is positioned when elevated during a stride, relative to a surface upon which the foot will engage.

The manipulators may be implemented in a variety of manners. In some embodiments, the manipulators lock the prosthetic foot in place after manipulating the prosthetic foot about the axes and while the sensed movement characteristics indicate that the prosthetic foot is elevated over the surface. The prosthetic foot may be maintained locked in place while the prosthetic foot is in contact with the surface and under load. For instance, surfaces of the respective manipulators may lock in response to pressure corresponding to a user bearing weight upon the prosthetic foot as it is engaged with the ground. In response to the sensed movement characteristics indicating that the prosthetic foot has been lifted from the surface and is not under load, the manipulators unlock and further manipulate the prosthetic foot about the first and second axes (e.g., for positioning as above). In this context, the manipulators can operate to respectively position, lock and re-position a prosthetic foot during the course of a user's stride. This can be implemented in a training setting to generate perturbations that challenge the user to improve balance, or in a walking setting (or jogging/running) in which the prosthetic foot is positioned to enhance the user's body control.

In various embodiments, each manipulator has surfaces that are maintained in an interface position while the manipulators are moved (e.g., rotated) to impart positioning relative to an incline of the surfaces. For instance, where each manipulator rotates independently from one another, each surface can be implemented with an inclined plane with one manipulator rotating along an axis fixed relative to a patient's leg, and the other manipulator rotating along an axis fixed relative to a foot component. The manipulators can thus be operated with the foot component, such that the axis fixed relative to the foot component is oriented vertically relative to ground when the foot component is used in a standing pose and flat on the ground. In various such embodiments, the respective surfaces can create a moment tending to rotate each of the surfaces along its respective axis due to contact force, and to hold the surfaces in place via friction between the surfaces.

Various embodiments are directed to enhancing the ability of a user to move, such as during walking or running. In some embodiments, the sensor circuit noted above predicts future movement of the prosthetic foot relative to an underlying surface based on the sensed movement characteristics detected over time. The prosthetic foot can then be manipulated about the respective axes based on the predicted future movement of the prosthetic foot.

Sensor circuits, control circuits and/or mechanical drive circuits as noted herein can be implemented with a processor or processors that utilize sensed characteristics along with special programming to carry out operations that produce a signal or other output that causes movement of manipulators as characterized herein. Such outputs may, for example, be mechanical outputs that cause movement of the manipulators, or an electrical output that is used to control movement within the manipulators. In this context, various embodiments include a motor or motors that drive one or more actuators or manipulators as separate components or integrated within. Heel position (or a change therein) can be mapped to motor position (or a change therein), and the motor can be adjusted accordingly. In some embodiments, a sensor circuit as above includes a processing circuit that predicts future movement of a prosthetic foot by executing an algorithm with the sensed movement characteristics as inputs to the algorithm, and that controls movement of the prosthetic foot by generating and outputting a respective control signal for each of the respective manipulators. The actuators and/or manipulators are responsive to the respective control signals by respectively manipulating the prosthetic foot, such as to adjust heel height or position relative to a ball region of the prosthetic foot, and/or about respective axes. For instance, when a user is accelerating or decelerating, the heel height can be adjusted accordingly. Where adaptation relative to an inclined surface is desired, an inclined posture can be applied to a prosthetic foot by adjusting manipulators that operate to effect angular positioning of the foot relative to an ankle connected to the lower leg.

Power for embodiments herein can be provided by a battery circuit. Such a circuit can be implemented within an actuator, manipulator, drive component and/or sensor. As noted herein, the power used in this context can be held relatively low by manipulating the prosthetic foot in conditions in which the foot is not under a load.

Motion mapping or estimation can be carried out in a variety of manners. In some embodiments, a state estimation and control flow is as follows, as may be implemented in various use-case and/or experimental type approaches:

Level 1: Sensor measures Physical movement of the foot
Signal 1-2: Sensor measurements: Angular velocity, Acceleration
Level 2: Strap-down integration of inertial signals (Pedestrian Dead-Reckoning)
Signal 2-3: World-frame acceleration, velocity, position, orientation
Level 3: Stride segmentation at foot lift-off
Signal 3-4: Stride length, stride time, and speed estimate of each stride. Swing/stance flag.
Level 4: Gait characterization (e.g., speed averaging, activity classification)
Signal 4-5: Average speed (n strides average)

Activity Identified (e.g., walking, running, jogging, ramp, stairs)

Level 5: Map activity & speed to prosthesis parameter settings (e.g., heel height, stiffness, ankle angle)

Levels 6 (multiple): Control device actuators to achieve desired parameters (swing, motor PWM (pulse-width modulation)/voltage, stance, hydraulics).

Other inputs, such as EMG signals, commands from a brain-computer interface, or commands or tuning from an off-board controller/tuner such as a phone app can be implemented. A variety of parameter mappings may be utilized, for use-case and/or experimental type approaches, including one or more of the following (which may utilize parameters that are altered, reversed (inversely proportional), replaced with other functions (quadratic, cubic, etc.), made constant, or otherwise varied).

1) Heel height proportional to running speed. Fully extended (down) at 1.5 m/s, fully retracted at 4.5 m/s
2) Ankle angle proportional to running speed. 90 degrees to leg (nominal condition) at 1.8 m/s, 10 deg plantarflexed at 4.8 m/s
3) Stiffness proportional to running speed. 7 N/mm at 1.5 m/s, 25 N/mm at 5.0 m/s.
4) Stiffness reduced when ascending stairs, increased when descending stairs
5) Ankle dorsiflexed (toes up) when ascending stairs, plantarflexed (toes down) when descending stairs.
6) Heel down when climbing stairs, heel up when descending stairs (degree to be determined).

As may be implemented in accordance with one or more embodiments, an apparatus (and/or related method) is employed for facilitating use of a prosthetic foot, and provides movement of a heel region relative to a ball region of the prosthetic foot. Such a prosthetic foot includes a front ball region and a rear heel region for respectively contacting a surface along which a user of the prosthetic foot is travelling. The apparatus includes a mechanical actuator, a sensor circuit and a control circuit, that operate together for positioning the prosthetic foot. The mechanical actuator may include one or more actuator components, and is operable to position the prosthetic foot based on inputs sent from the control circuit, such as electrical inputs that drive one or more motors with the mechanical actuator. The sensor circuit senses movement parameters pertaining to movement of the user. Such a circuit may include, for example, motion sensors for detecting movement, position sensors for detecting relative position of one or more components of the prosthetic foot, speed sensors (e.g., GPS-based), load sensors and others. The control circuit (e.g., a microchip) operates with the sensor circuit to determine a state of movement of the user, including a speed at which the user is travelling along the surface, based on the movement parameters sensed by the sensor circuit. This determination may be made, for example, using modelled or known movement patterns and comparing or otherwise using the patterns with the sensed movement parameters. The control circuit dynamically positions the prosthetic foot in response to the speed at which the user is travelling along the surface, by manipulating the mechanical actuator (e.g., via electrical inputs) to move the rear heel region relative to the front ball region based on changes in the speed. Various embodiments also include the prosthetic foot, and may further include a motor that moves the mechanical actuator to position the prosthetic foot, in response to inputs from the control circuit.

The control circuit operates with the sensor circuit to dynamically position the prosthetic foot in response to the speed at which the user is travelling along the surface, using one or more of a variety of approaches. For instance, the control circuit may be implemented to generate a real-time reconstruction of motion of the prosthetic foot based on the sensed parameters. The prosthetic foot can then be dynamically positioned based on the real-time reconstruction. In some embodiments, the control circuit manipulates the mechanical actuator to move the rear heel region toward or away from the front ball region, based on the changes in the determined speed. In other embodiments, the control circuit manipulates the mechanical actuator to increase or decrease the height of the rear heel region relative to the front ball region, based on the changes in the speed. Certain embodiments involve a combination of heel region height adjustment and adjustment of the distance between the heel region and the ball region. One or more such embodiments may involve shifting the center of pressure at which the prosthetic foot strikes the surface, based on the determined speed. Other positioning may also be effected independent from or in conjunction with the above, such as to lengthen the effective length of the user's leg (including the prosthetic foot). In some embodiments, the control circuit operates with the sensor circuit to dynamically position the prosthetic foot under conditions in which the prosthetic foot is not under load, and to lock the prosthetic foot in position under conditions in which the prosthetic foot contacts the surface. The sensed movement parameters can be used to identify periods during which the prosthetic foot is not under load and periods during which the prosthetic foot is under load, with the positioning or locking of the prosthetic foot being carried out based on the identified periods.

In some embodiments, the control circuit operates with the sensor circuit to dynamically position the prosthetic foot in response to the speed at which the user is travelling along the surface, by manipulating the mechanical actuator to gradually eliminate the heel region from contributing to contact between the prosthetic foot and ground as the speed increases (e.g., by raising the heel region relative to the ball region with increasing speed, as noted herein). In these and/or other embodiments, the control circuit operates with the sensor circuit to dynamically position the prosthetic foot by manipulating the mechanical actuator to move the ball region downward to promote a forefoot-striking running gait as the speed increases.

Embodiments involving heel height adjustment may be implemented in a variety of manners, to suit particular applications. In some embodiments, the control circuit operates with the sensor circuit to dynamically position the prosthetic foot in response to the speed at which the user is travelling along the surface by manipulating the mechanical actuator to increase the height of the rear heel region relative to the front ball region as the speed increases, and to decrease the height of the rear heel region relative to the front ball region as the speed decreases. The mechanical actuator may, for example, include or employ a lever system that raises and lowers the heel region relative to the ball region.

Certain embodiments utilize a heel member and a ball member, respectively coupled to the heel region and the ball region, that support the user's weight when the prosthetic foot is in contact with the ground. The heel member is connected to the ball member at a joint, and the actuator increases or decreases the height of the rear heel region by pivoting the heel member relative to the ball member at the joint. The heel member and ball member may be implemented within a housing of the prosthetic foot, with the housing making the contact with the surface as supported by the heel member and ball member. Accordingly, the heel member can be moved relative to the ball member, without necessarily otherwise driving motion of the entire prosthetic foot.

The actuator as noted in embodiments above can be implemented with a variety of components. In some implementations, the actuator includes a screw mechanism affixed to a ball member and to a heel member as noted above. The screw mechanism operates to pivot the heel member relative to the ball member via actuation of a screw. Other embodiments involve respective manipulators that operate relative to one another to adjust positioning of the prosthetic foot, and can be implemented as characterized below and in the related figures.

Certain embodiments further involve altering stiffness of one or more regions of the prosthetic foot that makes contact with the surface. For instance, the control circuit as noted above can be implemented with the sensor circuit to manipulate the mechanical actuator to alter the stiffness of the at least one region of the prosthetic foot based on the determined speed. This approach may facilitate desired interaction between the prosthetic foot and the surface.

One or more embodiments may be implemented for altering the effective length of the user's leg, where the effective length refers to the length of the user's leg that includes the prosthetic foot. A control circuit as noted herein may be implemented with a sensor circuit to manipulate the mechanical actuator to alter the effective length of the user's leg, based on the sensed movement parameters. Accordingly, the effective length can be increased or reduced to suit particular applications.

In some embodiments, a control circuit as noted herein is configured and arranged to predict future movement of the prosthetic foot relative to the surface based on the sensed movement parameters detected over time. The position of the prosthetic foot is then manipulated based on the predicted future movement of the prosthetic foot.

In certain embodiments in which a user has two prosthetic feet, heel region positioning relative to ball regions in each prosthetic foot can be adjusted relative to the other prosthetic foot. For instance, changes in heel height, heel-to-ball distance, and effective leg length can be implemented in accordance with related changes in respective prosthetic feet.

Turning now to the Figures, FIG. 1 shows a prosthetic foot apparatus 100, in accordance with the present invention. The apparatus 100 includes a ball (or forefoot) member 110 and a heel member 120, coupled by an actuator 130. The actuator includes a screw 132 that operates to move the heel member 120 relative to the ball member 110, as driven by a motor 134. A controller circuit 136 utilizes motion parameters sensed by a sensor circuit 138 to determine desired positioning of the heel member 120 relative to the ball member 110, based on a speed that the user of the prosthetic apparatus 100 is moving. The controller circuit generates an output to control actuation of the screw 132 to achieve the desired positioning.

An upper region 112 of the apparatus 100 can be connected to a user's leg. The apparatus 100 in FIG. 1 may be attached to an existing running-specific prosthesis to produce a hybrid system. The apparatus may be provided as an integrated design as well, with variations in the nature of the actuator 130 and its respective connection to the ball member and heel member.

The controller circuit 136 and sensor circuit 138 can be implemented using a variety of different types of circuitry. For instance, the controller circuit 136 may be implemented with a microcontroller or other computing circuit programmed to process inputs from the sensor circuit 138 to generate an output signal that causes actuation of the actuator to move the heel region relative to the ball region. In certain embodiments, the controller circuit includes a microcontroller or other computing circuit that generates a map of movement of the prosthetic foot, based on inputs from the sensor circuit 138. In various implementations, the controller circuit 136 and/or the sensor circuit 138 are integrated with the prosthetic apparatus 100. For instance, one or both may be integrated within and/or on the actuator 130. In other implementations, the controller circuit and/or the sensor circuit 138 are positioned remote from the prosthetic apparatus, such as with the leg of the individual using the prosthetic apparatus 100. Power may be provided by a battery integrated with each sensor and/or otherwise coupled to provide power there to, which also may be provided to the motor 134. Such a battery may be integrated within the actuator 130.

FIGS. 2-10B show other prosthetic foot apparatuses, which may be implemented in a manner similar to that characterized with FIG. 1, with respective actuator components, control circuits and sensor circuits. Further, componentry such as motors, solenoids and springs that facilitate actuation may be implemented with the embodiments shown. For simplicity and clarity in viewing, various ones of these figures are shown with actuators and respective heel/ball members, with the understanding that actuator components (e.g., a motor), control circuit and sensor circuits may be implemented accordingly.

Figure 2:
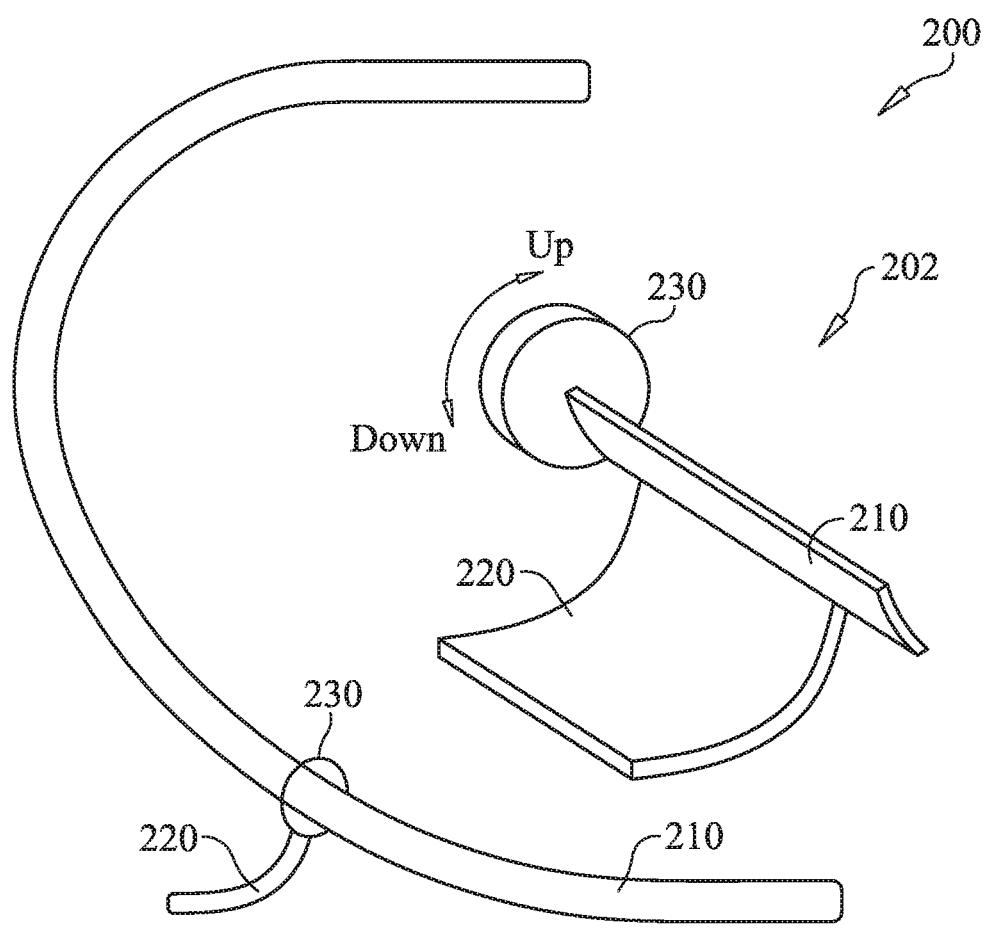
FIG. 2 shows another prosthetic foot apparatus, in accordance with the present invention.

Beginning with FIG. 2, another prosthetic foot apparatus 200 is shown, in accordance with the present invention. The apparatus 200 includes a ball member 210, heel member 220 and actuator 230. Inset 202 shows these components, with actuator 230 operating to rotate the heel member 220 as shown (up/down with clockwise/counter-clockwise rotation), as may be driven by a motor.

Figure 3:
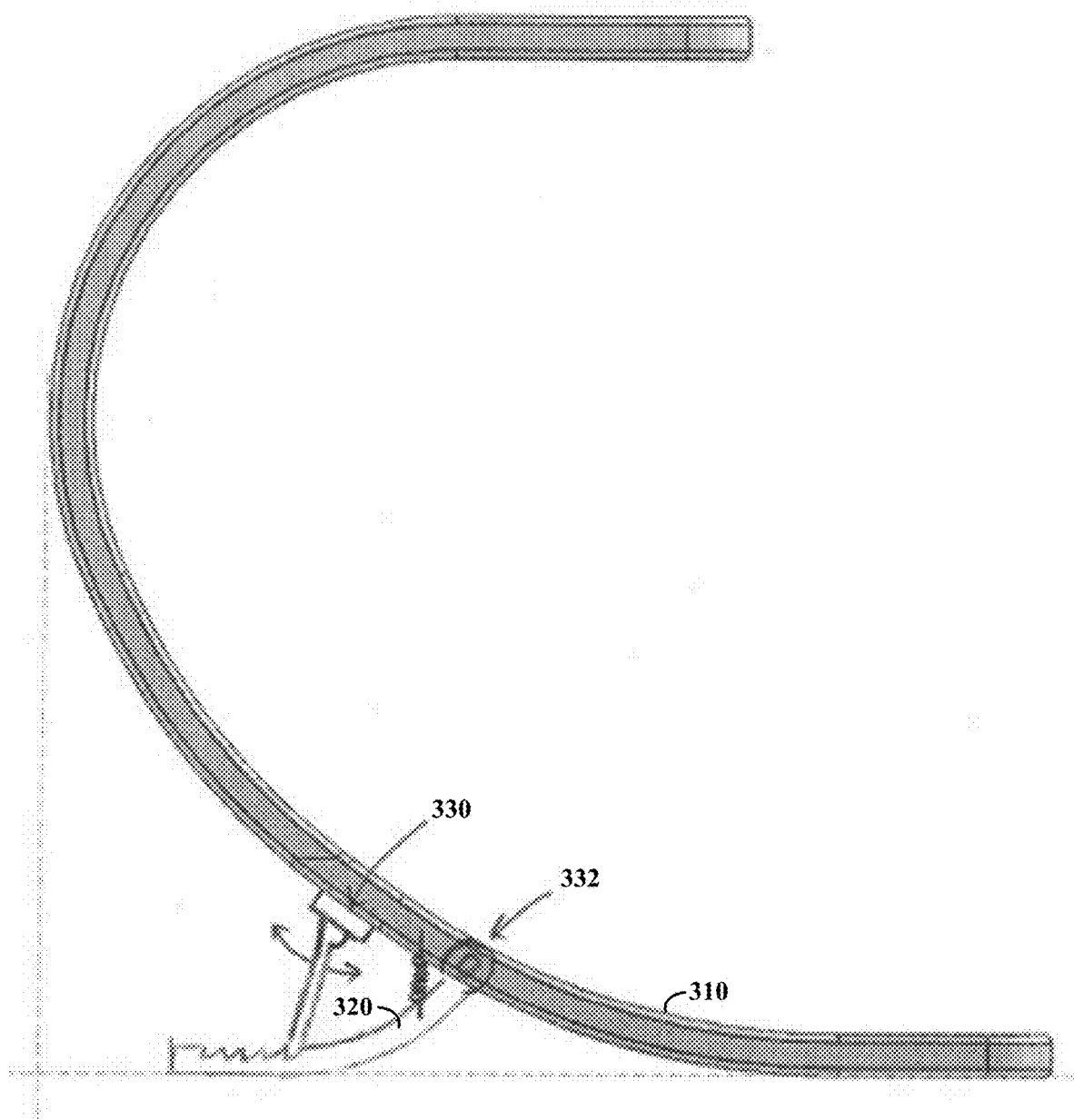
FIG. 3 shows another prosthetic foot apparatus, in accordance with the present invention.

FIG. 3 shows another prosthetic foot apparatus 300, in accordance with the present invention. The apparatus 300 includes a ball member 310, heel member 320, and actuator componentry 330 and 332. A motor or solenoid can be implemented with the actuator component 332 to move the heel member 320, with actuator component 330 being rotated to a position for locking the heel member 320.

Figure 4:
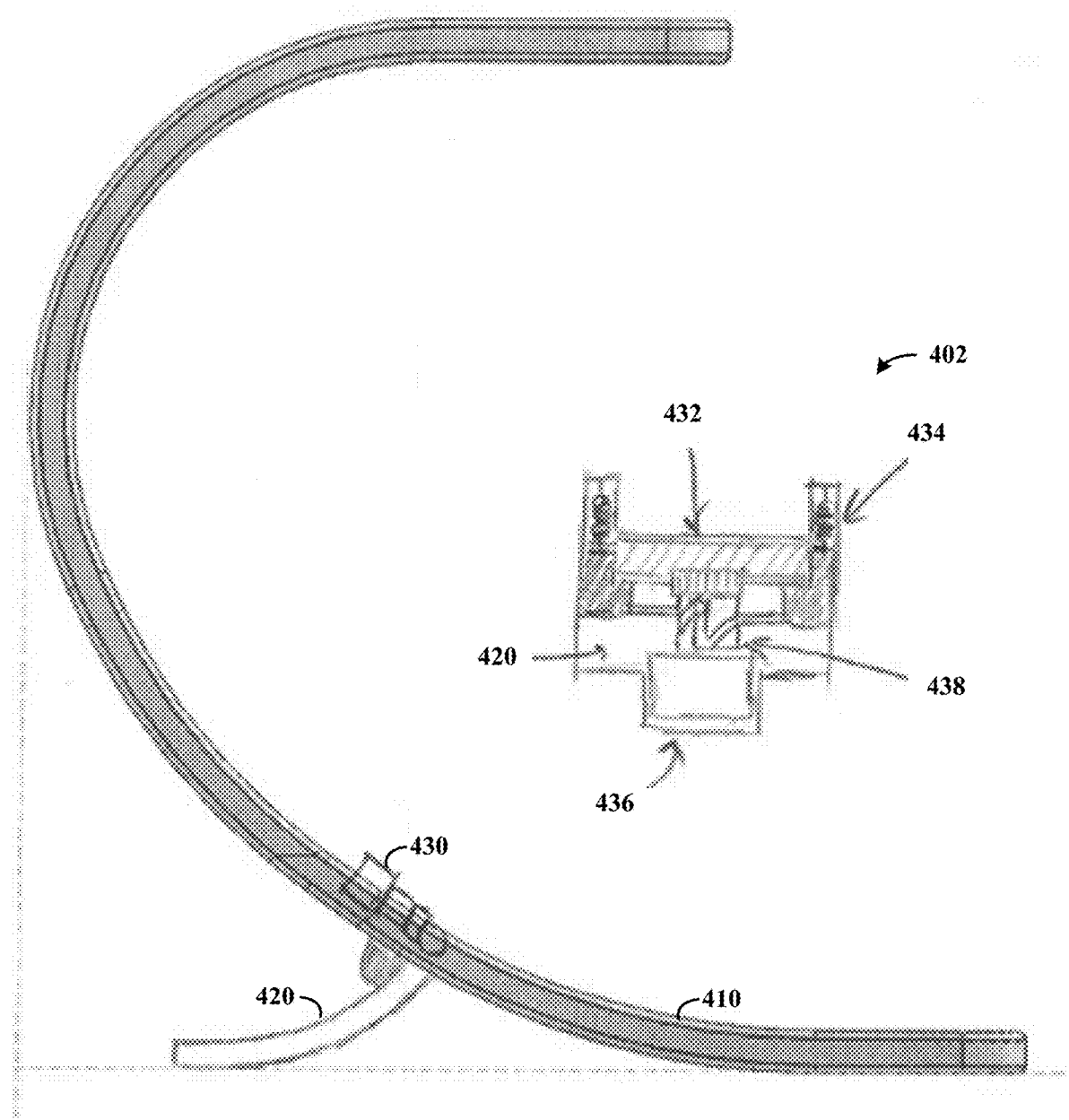
FIG. 4 shows another prosthetic foot apparatus, in accordance with the present invention.

FIG. 4 shows another prosthetic foot apparatus 400, in accordance with the present invention. The apparatus 400 includes a ball member 410, heel member 420, and actuator 430. Inset 402 shows an example implementation of the actuator 430, including a worm gear 432, tension springs 434, motor 436 and a barrel cam 438 that retracts (e.g., for coupling to shock absorbers that absorb shock in the heel member 420).

Figure 5:
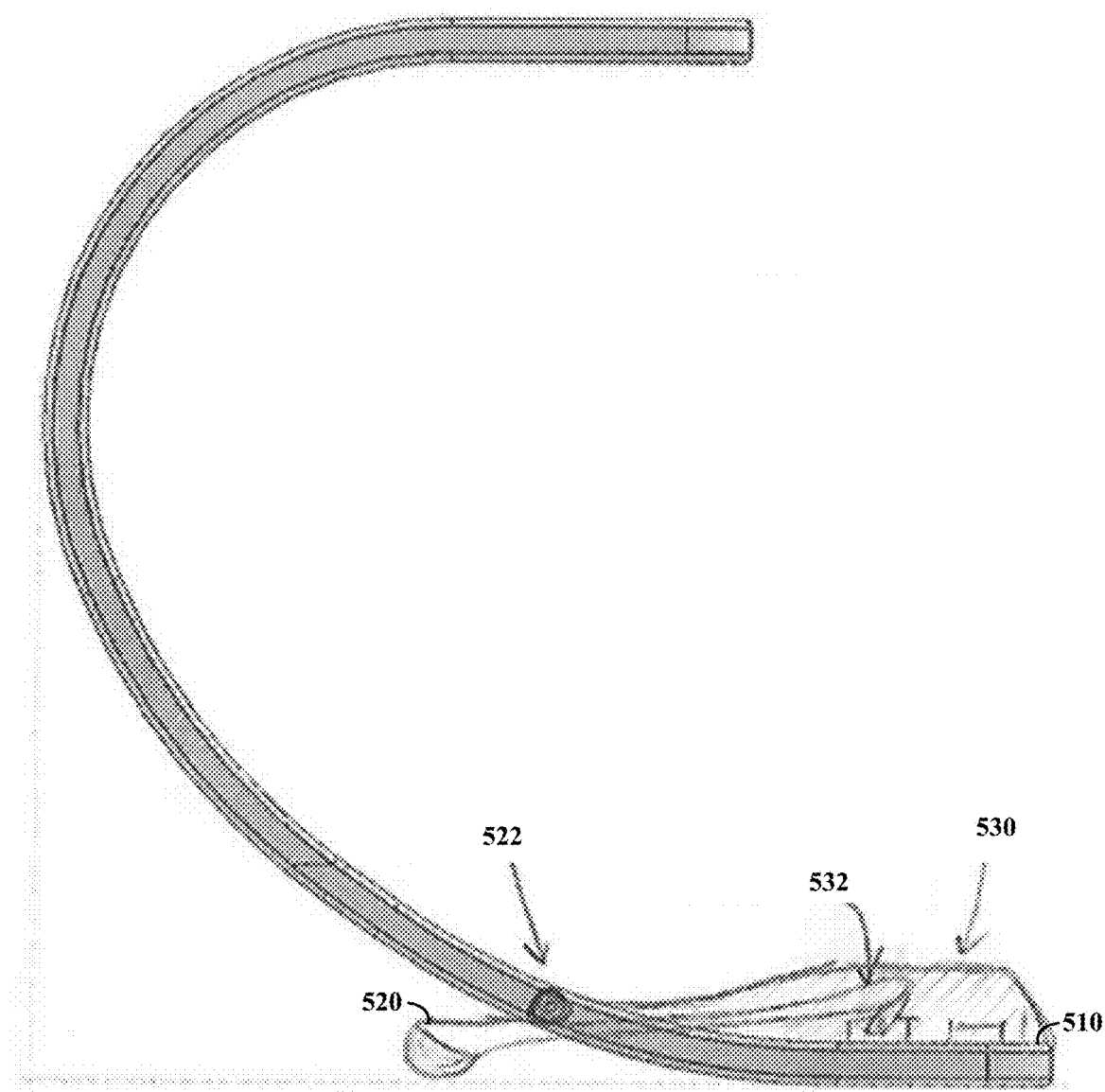
FIG. 5 shows another prosthetic foot apparatus, in accordance with the present invention.

FIG. 5 shows another prosthetic foot apparatus 500, in accordance with the present invention. The apparatus 500 includes a ball member 510, heel member 520 and actuator 530. Bearing 522 facilitates movement of the heel member 520 relative to the ball member 510 to adjust a distance between the two. Impact upon the heel member 520 is applied through the bearing 522. A lever arm or other component at 532 within the actuator 530 operates to move the heel member 520 fore and aft to set the distance.

Figure 6:
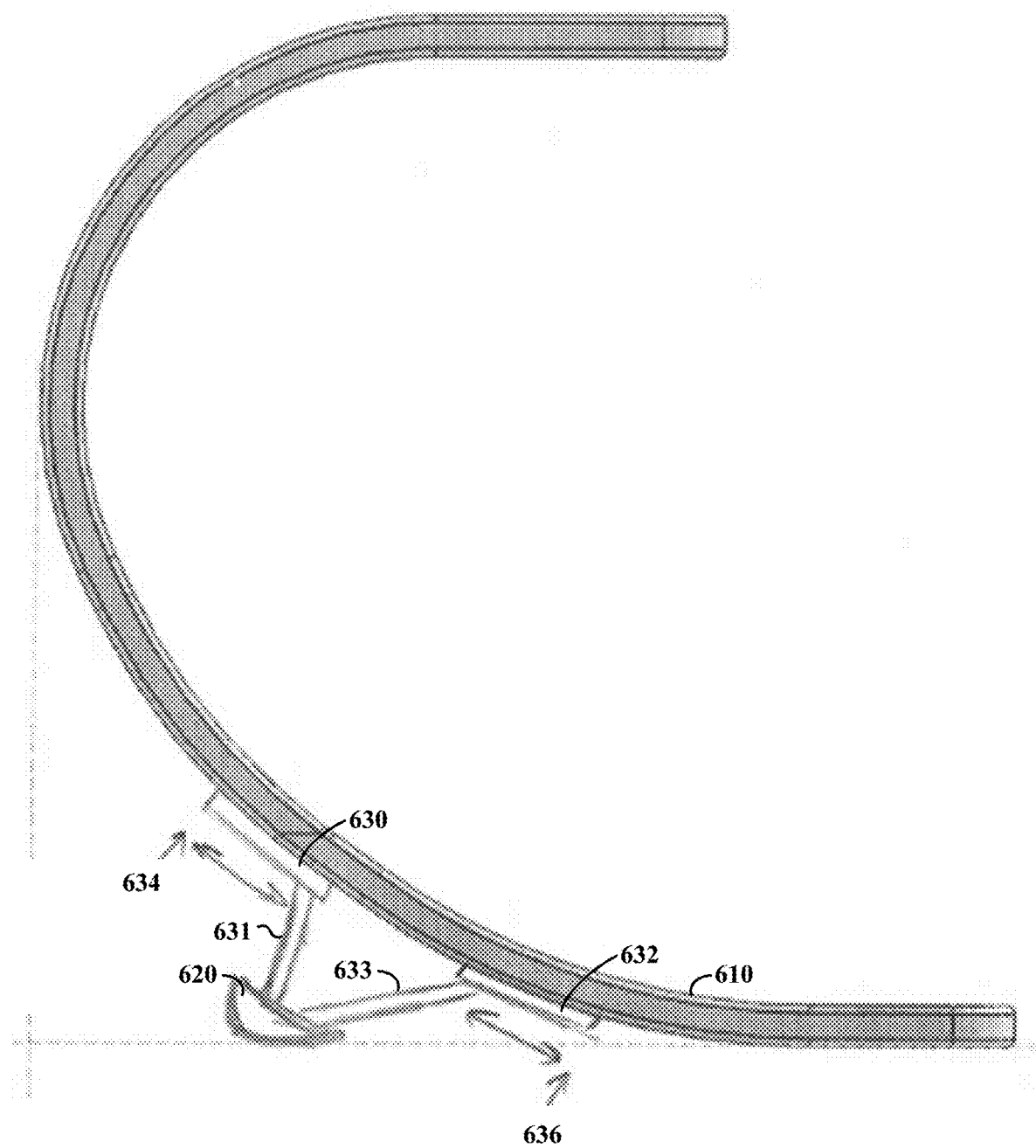
FIG. 6 shows another prosthetic foot apparatus, in accordance with the present invention.

FIG. 6 shows another prosthetic foot apparatus 600, in accordance with the present invention. The apparatus 600 includes a ball member 610, heel member 620, and actuator portions 630 and 632 coupled by struts 631 and 633 to the heel member. As shown, the heel member 620 is fully deployed. When struts 631 and 633 are in positions 634 and 636 respectively, the heel member 620 is fully retracted.

Figure 7:
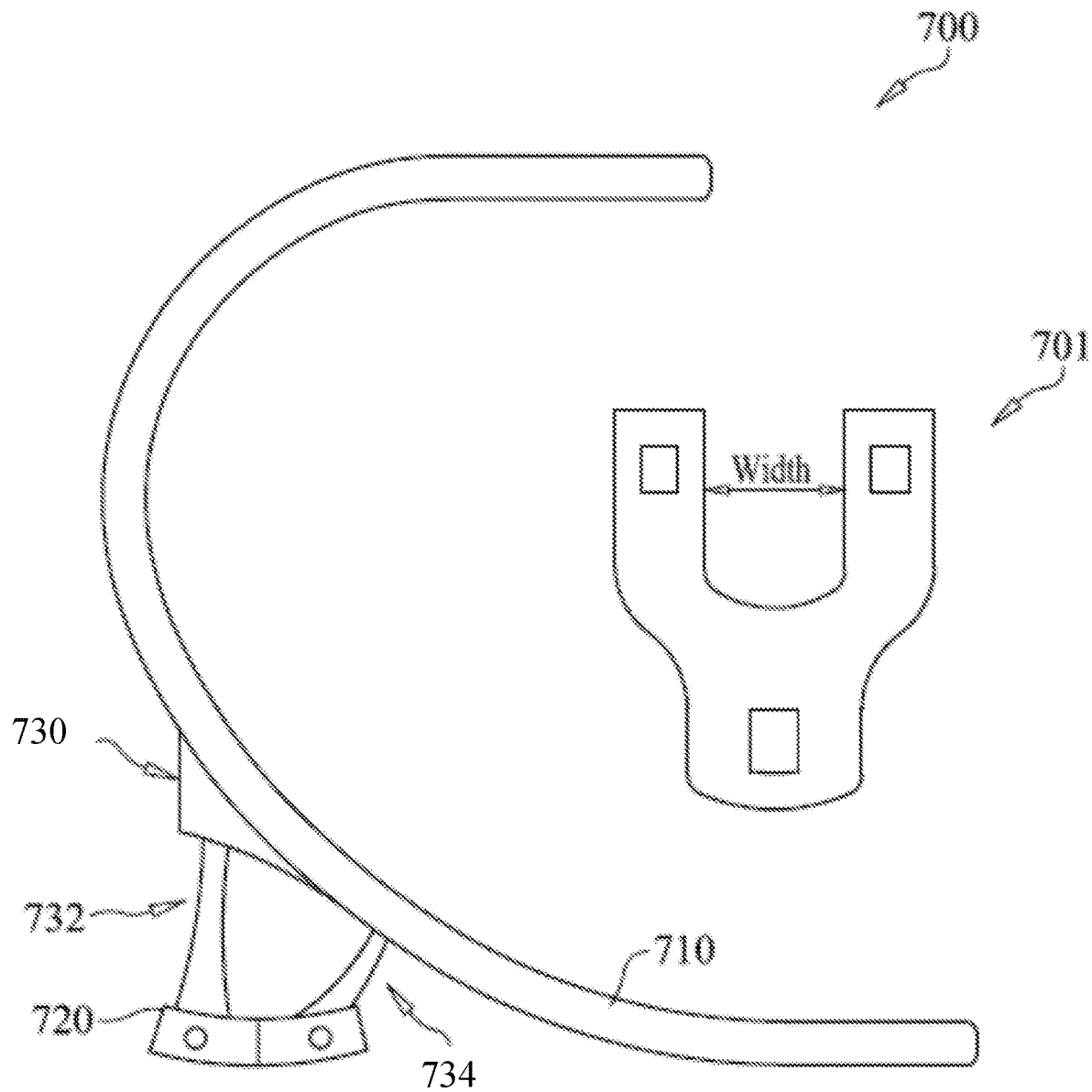
FIG. 7 shows another prosthetic foot apparatus, in accordance with the present invention.

FIG. 7 shows another prosthetic foot apparatus 700, in accordance with the present invention. The apparatus 700 includes a ball member 710, heel member 720, and actuator 730 coupled to the heel member by supports 732 and 734. A motor may be integrated within the actuator 730 and/or within the prosthetic apparatus 700. Inset 701 shows an example implementation of the heel member 720, from a top view. A locking mechanism and/or suspension components may be implemented within the actuator 730.

Figure 8:
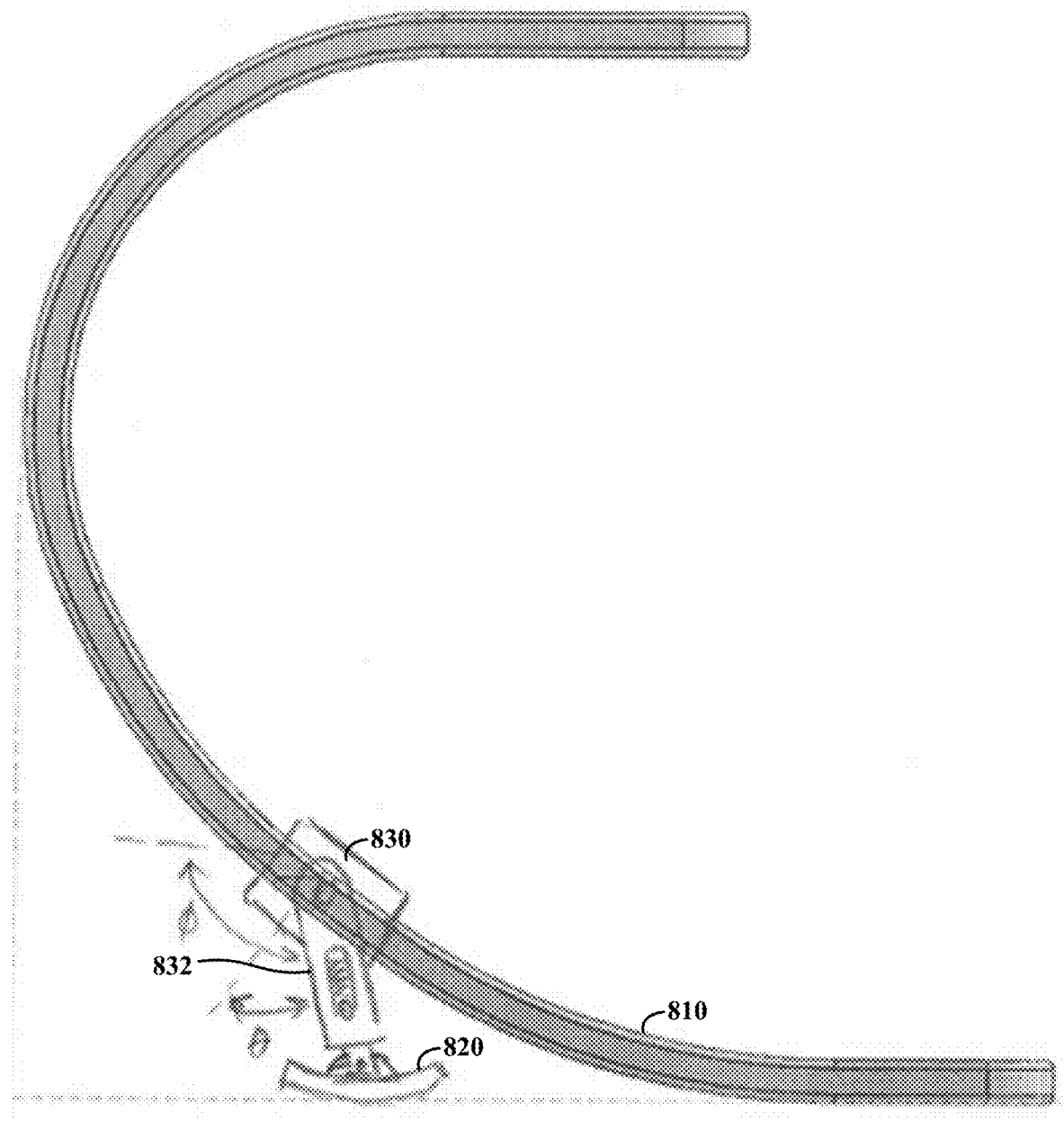
FIG. 8 shows another prosthetic foot apparatus, in accordance with the present invention.

FIG. 8 shows another prosthetic foot apparatus 800, in accordance with the present invention. The apparatus 800 includes a ball member 810, heel member 820, and actuator 830 that operates to move the heel fore and aft, and/or adjust the heel height, relative to the ball member 810. An actuator arm 832 pivots as shown to provide relative heel member movement. In some embodiments, a screw or other apparatus within the actuator arm 832 may adjust the height of the heel. In other embodiments, the actuator arm 832 includes shock absorbing componentry.

Figure 9:
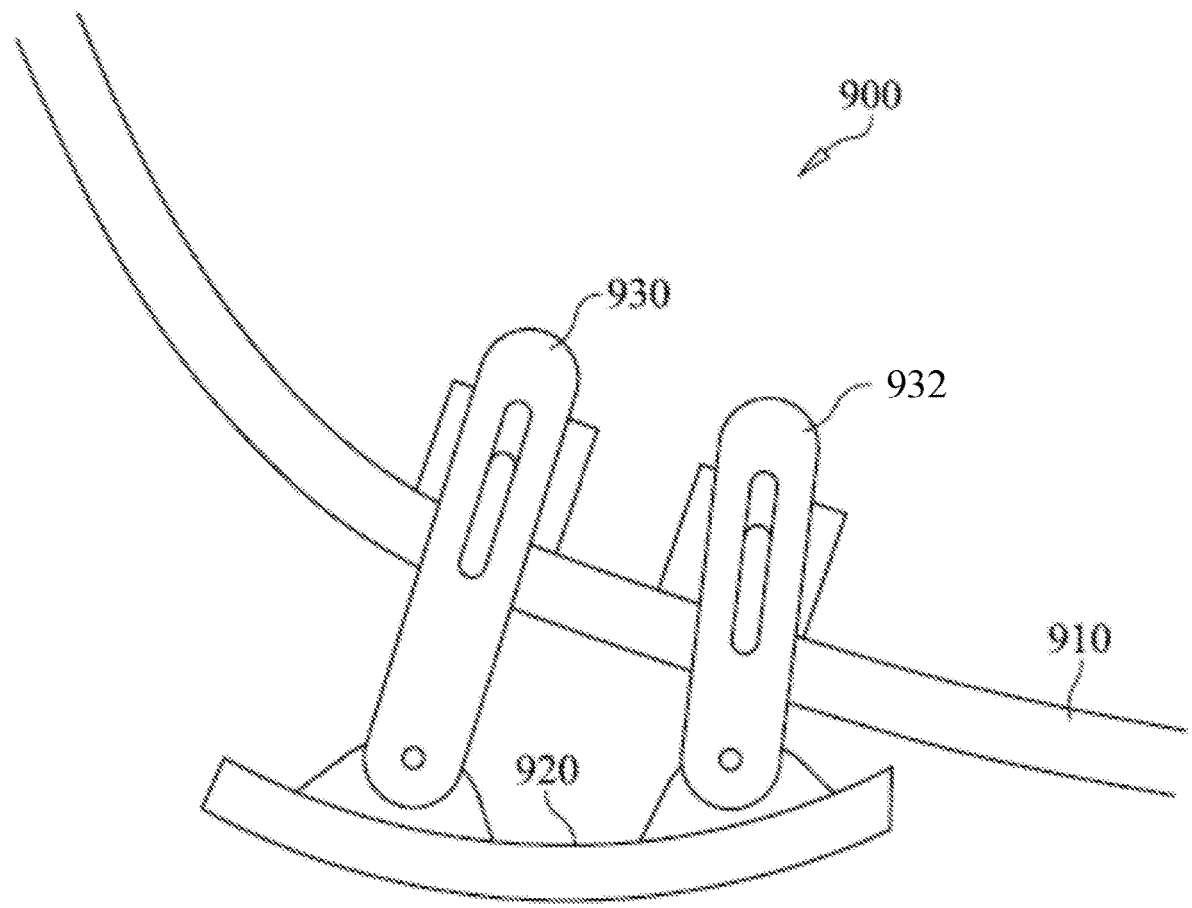
FIG. 9 shows another prosthetic foot apparatus, in accordance with the present invention.

FIG. 9 shows another prosthetic foot apparatus 900, in accordance with the present invention. The apparatus 900 includes a ball member 910, heel member 920, and respective actuators 930 and 932 that position the heel member 920. In some implementations, the actuators 930 and 932 provide independent suspension.

Figure 10A:
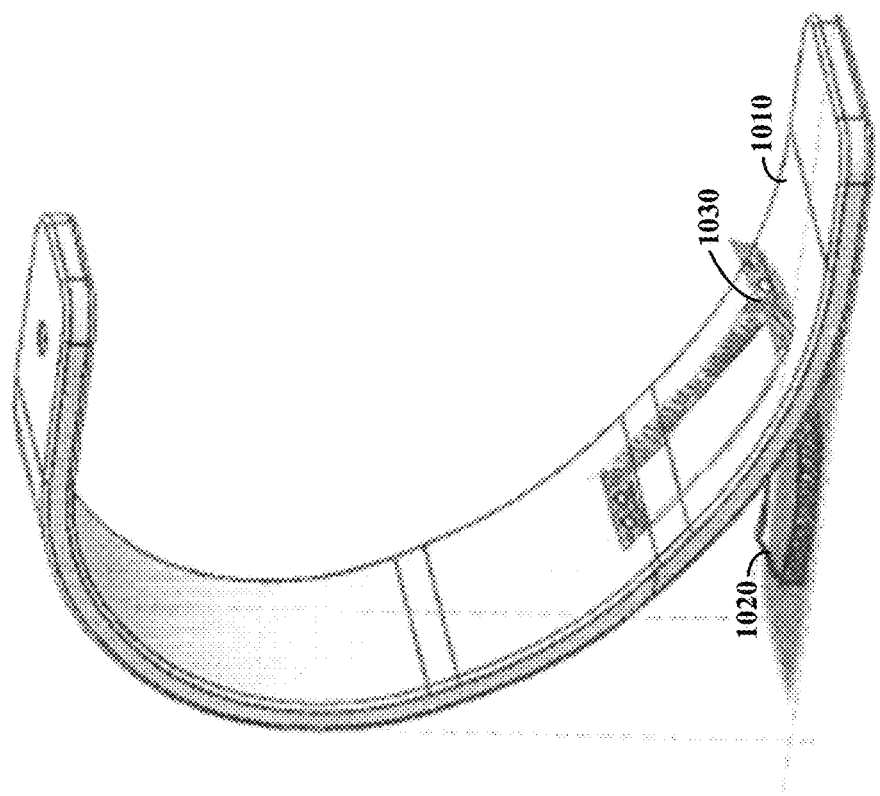
FIGS. 10A and 10B show respective views of another prosthetic foot apparatus, in accordance with the present invention.
Figure 10B:
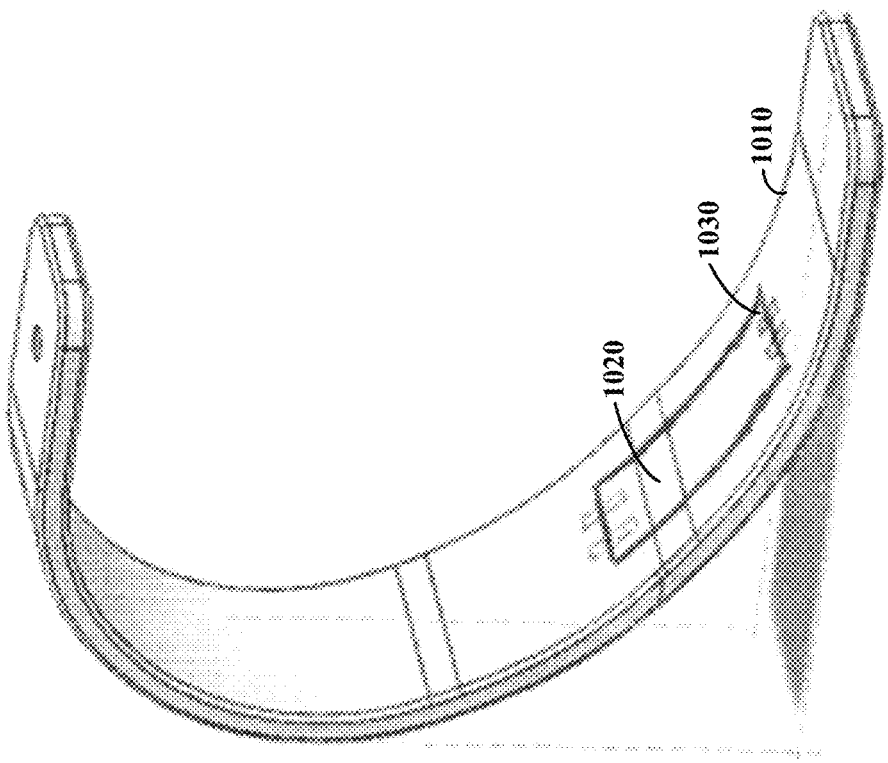

FIGS. 10A and 10B show respective views of another prosthetic foot apparatus 1000, in accordance with the present invention. The apparatus 1000 includes a ball member 1010, heel member 1020, and actuator 1030. FIG. 10A shows the apparatus 1000 with the heel member 1020 in a retracted position, in-line with the contour of the ball member 1010. FIG. 10B shows the apparatus 1000 with the heel member 120 in an extended position, lowered relative to the ball member 1010.

Figure 11:
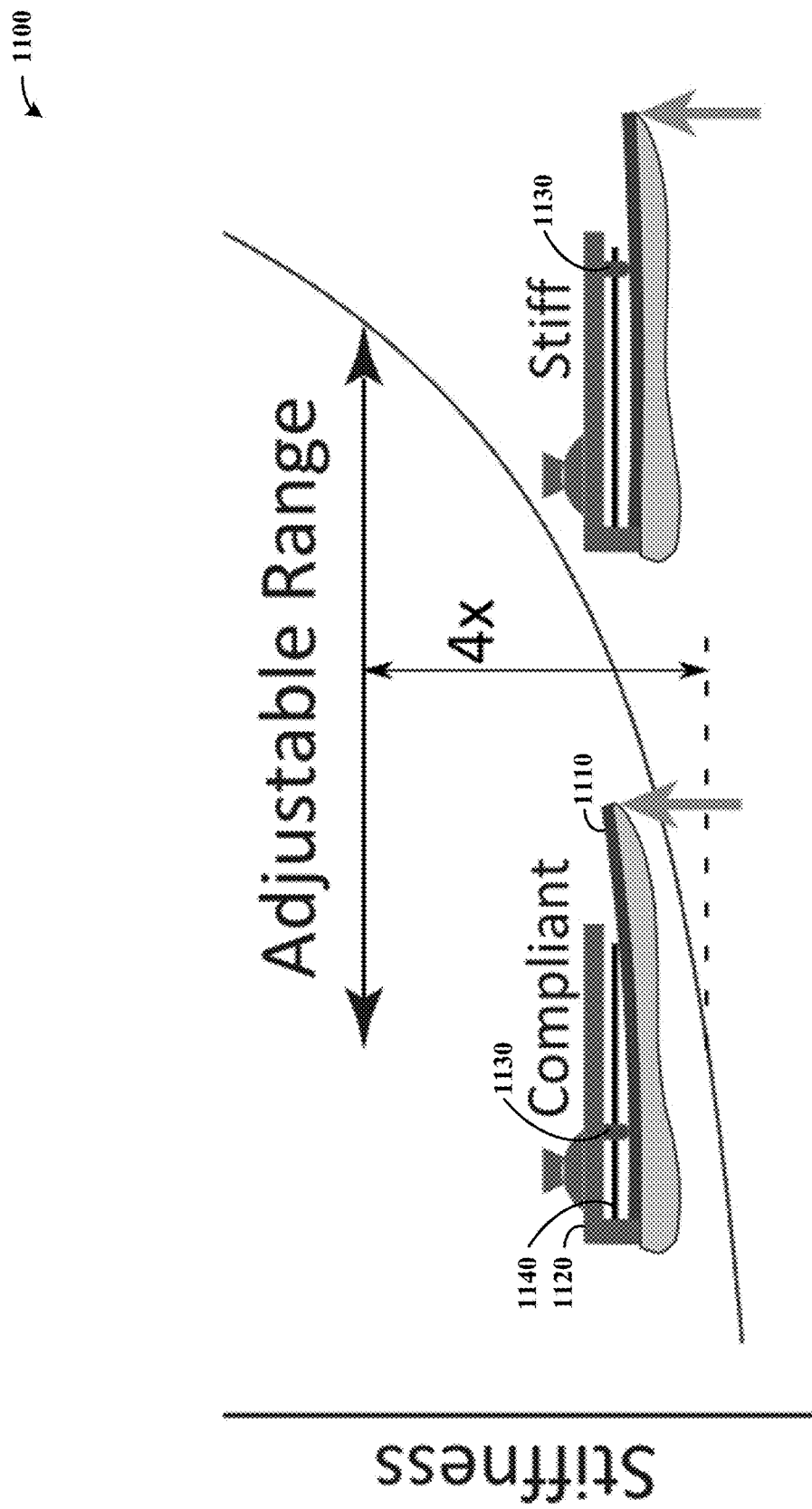
FIG. 11 shows a prosthetic foot apparatus for controlling foot stiffness, in accordance with the present invention.

FIG. 11 shows a prosthetic foot apparatus 1100 for controlling foot stiffness, in accordance with the present invention. The apparatus 1100 is shown in two positions for providing stiffness to foot portion 1110, respectively labeled compliant and stiff. A support structure 1120 supports a fulcrum 1130 and a stiffening structure 1140. In the compliant position, the fulcrum 1130 is positioned near the heel. In the stiff position, the fulcrum 1130 is positioned near the toe. A plot is overlaid upon the figure, and shows increasing stiffness with increased fulcrum position (from left to right). Accordingly, the stiffness can be suddenly or gradually adjusted, such as to accommodate differences between walking and running and/or differences across walking or running speed. The stiffening structure 1140 may, for example, be implemented with a leaf spring keel.

Figure 12:
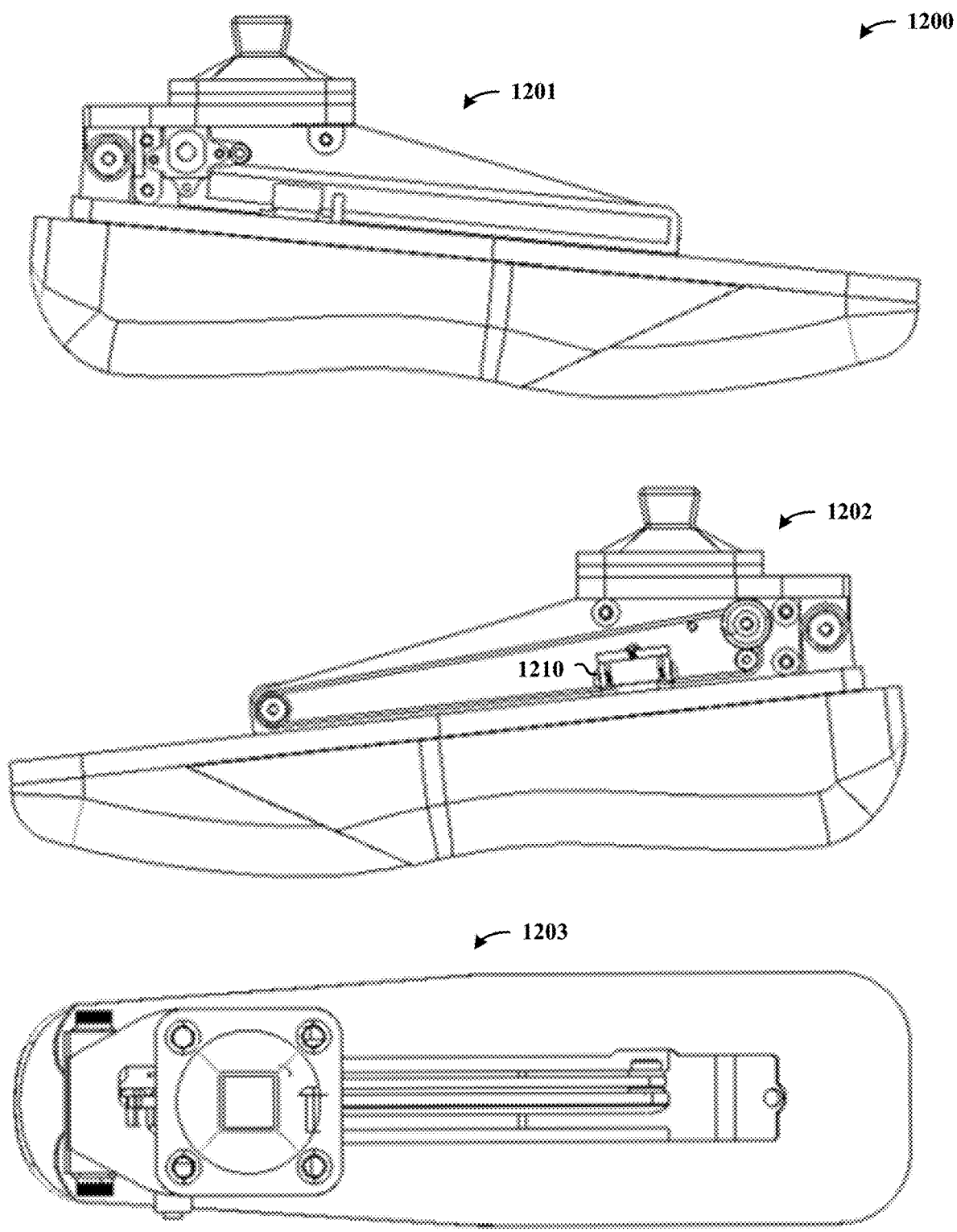
FIG. 12 shows respective views of a prosthetic foot apparatus for controlling stiffness, in accordance with the present invention.

FIG. 12 shows respective views of a prosthetic foot apparatus 1200 for controlling stiffness, in accordance with the present invention. Right view 1201, left view 1202, and top view 1203 are shown. A fulcrum component 1210 can be adjusted fore and aft, to provide controlled stiffness in a manner such as shown in FIG. 11.

Figure 13A:
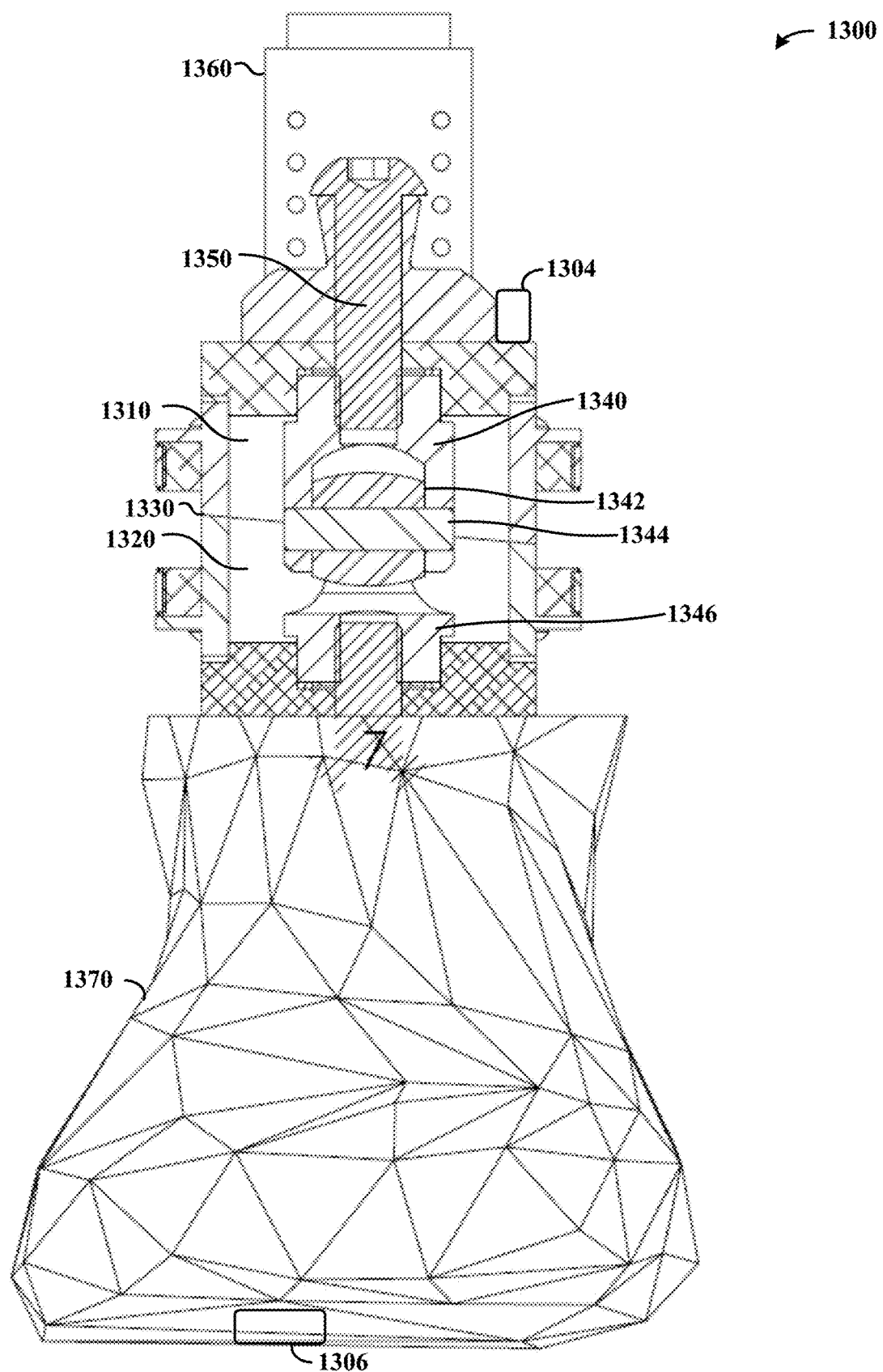
FIG. 13A shows a front view of a prosthetic apparatus in accordance with the present invention.
Figure 13B:
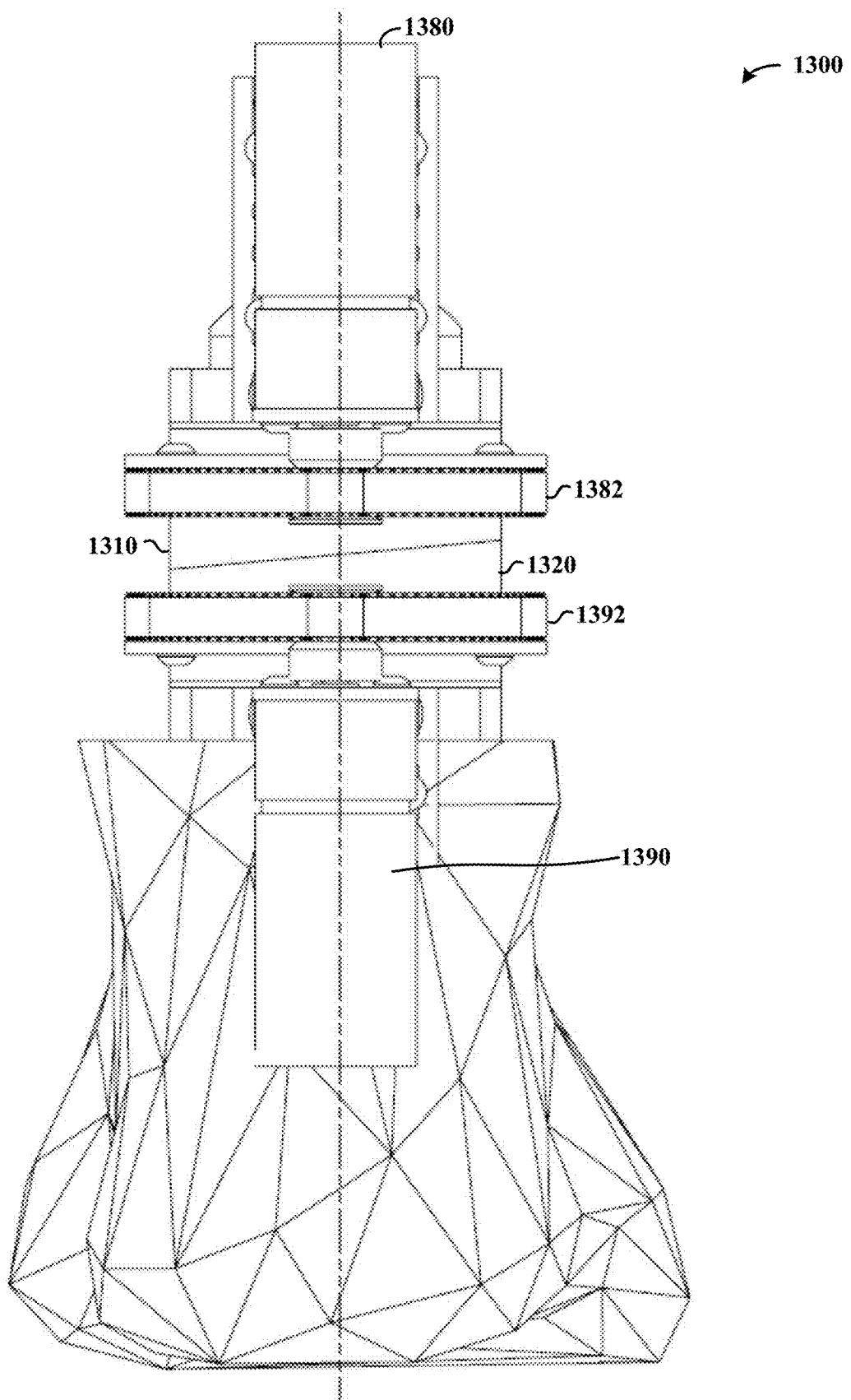
FIG. 13B shows a back view of a prosthetic apparatus in accordance with the present invention.

FIGS. 13A and 13B show front and back views of a prosthetic apparatus 1300 in accordance with the present invention. Referring to FIG. 13A, upper and lower manipulators respectively have an upper angle-cut cylinder 1310 and a lower angle-cut cylinder 1320 that interface at 1330 along respective surfaces. A universal-type joint works to maintain the surfaces in contact and restrain the foot from twisting about the leg axis, and includes an upper block 1340, spider/coupler 1342, central pin 1344 and lower block 1346. These components are shown by way of example, and can be implemented using a variety of different types of joints/coupling.

The prosthetic apparatus 1300 may further include componentry 1360 that couples to a user's leg, and/or a prosthetic foot 1370. A fastener 1350 such as a bolt can be used to couple to componentry 1360, which can be fixed relative to a user's leg. A variety of fasteners, prosthetics, and other componentry can be implemented to suit particular embodiments.

FIG. 13B shows the cylinders 1310 and 1320 from a back view relative to prosthetic foot 1370. By way of example, external mechanical drive components 1380 and 1390 are also shown coupled to rotate each cylinder via drive belts 1382 and 1392. Such an approach may be implemented, for instance, in a training or laboratory setting. Other drive components may be implemented with the apparatus 1300, such as via direct-drive motors integrated within and/or coupled to the cylinders, other indirect-drive components, screw drives, and others.

Various other componentry can be implemented with prosthetic apparatuses as characterized herein. Referring again to FIGS. 13A and 13B by way of example, sensors can be implemented to sense force, load, position, acceleration, movement and other characteristics. These sensors can be coupled to (or integrated with) control circuitry that operates to drive respective manipulators for positioning the prosthetic foot. By way of example, a sensor 1304 can be implemented to sense motion, images (e.g., ground profile), elevation, angle relative to ground and/or other conditions. These sensed conditions can be used to manipulate the cylinders 1310 and 1320 (e.g., by passing signals to a controller circuit and/or motor that drives the cylinders to rotate). In this context, a controller circuit can be implemented within the manipulators, or with external mechanical drive components such as shown in FIG. 13B. Similarly, a sensor 1306 may be implemented to sense force in the position as shown (in the bottom of prosthetic foot 1370) or in another area of the apparatus that is subjected to force when a user of the prosthetic foot 1370 is applying body weight thereto. The sensor 1306 may also be implemented to sense characteristics noted above as being implemented with sensor 1304.

Figure 14:
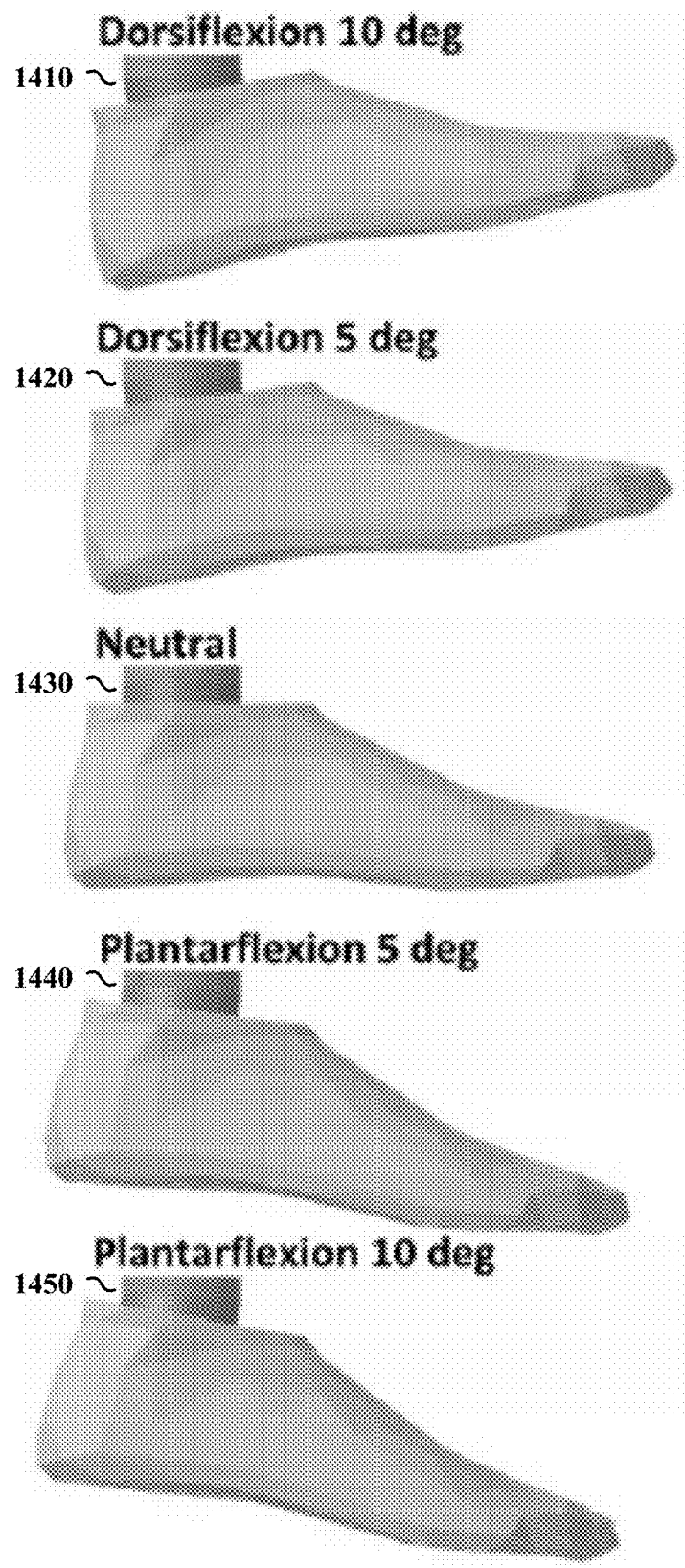
FIG. 14 shows a prosthetic apparatus at various positions, in accordance with one or more embodiments.
Figure 15:
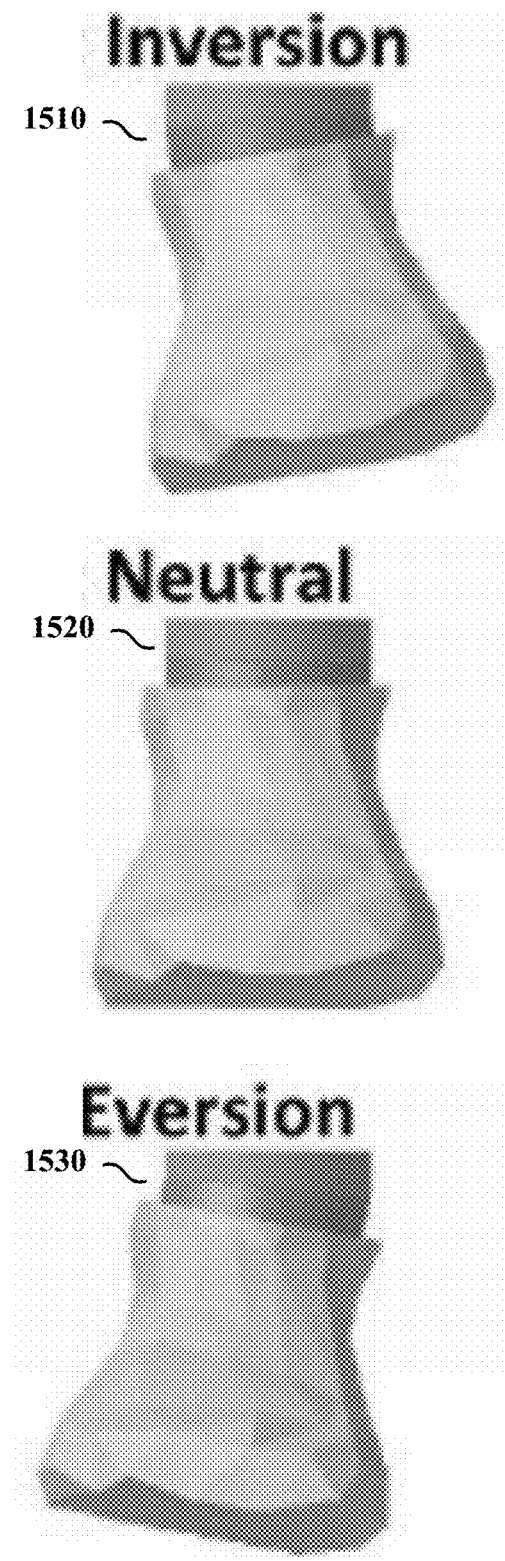
FIG. 15 shows a prosthetic apparatus at various positions, in accordance with one or more embodiments.

FIGS. 14 and 15 show prosthetic apparatuses at various positions, in accordance with one or more embodiments. The embodiments shown may, for example, be implemented with respective manipulators as shown in FIGS. 13A-13B. Beginning with FIG. 14, respective interfacing manipulators are shown at 1410 and 1420 respectively positioned to provide 10 degrees and 5 degrees of dorsiflexion for a prosthetic foot. The manipulators are shown at 1430 to provide a neutral position, and at 1440 and 1450 to respectively provide 5 and 10 degrees of plantarflexion. In FIG. 15, the manipulators are shown at an inversion position 1510, neutral position 1520, and eversion position 1530.

Figure 16:
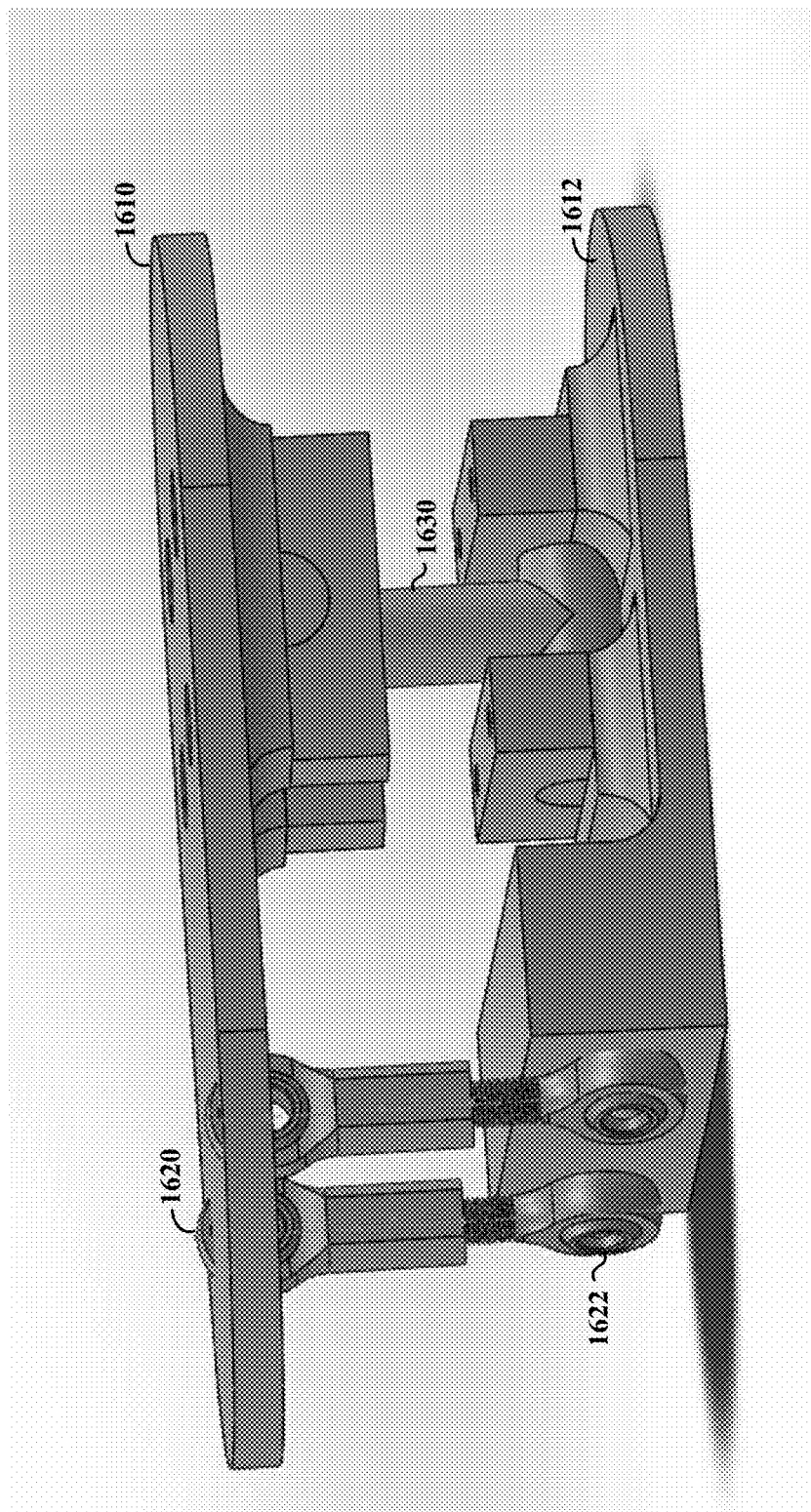
FIG. 16 shows a prosthetic apparatus, in accordance with another embodiment.

FIG. 16 shows a prosthetic apparatus 1600, in accordance with one or more embodiments. The apparatus 1600 includes two platforms 1610 and 1612, which can respectively be coupled to a prosthetic foot and a user's leg. By way of example, the platforms are shown coupled with tie rods at 1620 and 1622 (with an adjacent tie rod not labeled), and another pivoting rod 1630. In various implementations, the tie rods are replaced with power screws that spin to actuate the platforms relative to one another.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., sensing, generating a control signal for operating an actuator, or positioning a manipulator). For example, in certain of the above-discussed embodiments, one or more modules are discrete logic circuits or programmable logic circuits configured and arranged for implementing these operations/activities, such as with controllers or sensors that can be implemented with the apparatus(es) shown in the Figures. In certain embodiments, such a programmable circuit is one or more computer circuits programmed to execute a set (or sets) of instructions that control the alignment of a prosthetic foot. The instructions (and/or configuration data) can be in the form of firmware or software stored in and accessible from a memory (circuit). As an example, first and second modules may include a combination of a CPU hardware-based circuit and a set of instructions in the form of firmware, where the first module includes a first CPU hardware circuit with one set of instructions and the second module includes a second CPU hardware circuit with another set of instructions. Such instructions may also be implemented for training a user via the application of perturbations as discussed herein.

Certain embodiments are directed to a computer program product (e.g., nonvolatile memory device), which includes a machine or computer-readable medium having stored thereon instructions which may be executed by a computer (or other electronic device) to perform these operations/activities.

Based upon the above discussion and illustrations, those skilled in the art will readily recognize that various modifications and changes may be made to the various embodiments without strictly following the exemplary embodiments and applications illustrated and described herein. For example, additional actuators may be used to provide a further degree or degrees of freedom. Different types of heel members and ball members may be utilized to suit particular applications. Different angles of interface and different types of interfaces may be used to achieve prosthetic positioning. Further, other prosthetics may be similarly controlled, such as those pertaining to knee or hip movement. In addition, the various embodiments described herein may be combined in certain embodiments, and various aspects of individual embodiments may be implemented as separate embodiments. The various embodiments described herein may also be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
   a mechanical actuator configured and arranged to position a prosthetic foot having a front ball region and a rear heel region for respectively contacting a surface along which a user of the prosthetic foot is travelling, by moving the rear heel region relative to the front ball region;
   a sensor circuit configured and arranged to sense movement parameters pertaining to movement of the user; and
   a control circuit configured and arranged with the sensor circuit to
      determine a state of movement of the user, including a speed at which the user is travelling along the surface, based on the movement parameters sensed by the sensor circuit, and
      dynamically position the prosthetic foot in response to the speed at which the user is travelling along the surface, by manipulating the mechanical actuator to move the rear heel region relative to the front ball region while the user is travelling along the surface, based on changes in the speed.

2. The apparatus of claim 1, wherein the control circuit is configured and arranged with the sensor circuit to dynamically position the prosthetic foot in response to the speed at which the user is travelling along the surface, by manipulating the mechanical actuator to move the rear heel region toward or away from the front ball region, based on the changes in the speed.

3. The apparatus of claim 1, wherein the control circuit is configured and arranged with the sensor circuit to dynamically position the prosthetic foot in response to the speed at which the user is travelling along the surface, by manipulating the mechanical actuator to increase or decrease the height of the rear heel region relative to the front ball region, based on the changes in the speed.

4. The apparatus of claim 3, wherein the control circuit is configured and arranged with the sensor circuit to dynamically position the prosthetic foot in response to the speed at which the user is travelling along the surface by manipulating the mechanical actuator to increase the height of the rear heel region relative to the front ball region as the speed increases, and to decrease the height of the rear heel region relative to the front ball region as the speed decreases.

5. The apparatus of claim 3, wherein the mechanical actuator includes a lever system configured and arranged to raise and lower the heel region relative to the ball region and to lock the heel region in place.

6. The apparatus of claim 3, further including a heel member and a ball member, respectively coupled to the heel region and the ball region and configured and arranged to support the user's weight when the prosthetic foot is in contact with the surface, the heel member being connected to the ball member at a joint, the actuator being configured and arranged to increase or decrease the height of the rear heel region by pivoting the heel member relative to the ball member at the joint.

7. The apparatus of claim 6, wherein the actuator includes a screw mechanism affixed to the ball member and to the heel member, the screw mechanism being configured and arranged to pivot the heel member relative to the ball member via actuation of a screw.

8. The apparatus of claim 1, wherein the control circuit is configured and arranged with the sensor circuit to dynamically position the prosthetic foot under conditions in which the prosthetic foot is not under load, and to lock the prosthetic foot in position under conditions in which the prosthetic foot contacts the surface.

9. The apparatus of claim 8, wherein the control circuit is configured and arranged to use the sensed movement parameters to identify periods during which the prosthetic foot is not under load and periods during which the prosthetic foot is under load, and to dynamically position or lock the prosthetic foot based on the identified periods.

10. The apparatus of claim 1, wherein the control circuit is configured and arranged with the sensor circuit to dynamically position the prosthetic foot in response to the speed at which the user is travelling along the surface by manipulating the mechanical actuator to move the ball region downward to promote a forefoot-striking running gait as the speed increases.

11. The apparatus of claim 1, wherein
    the mechanical actuator is configured and arranged to alter stiffness of at least one region of the prosthetic foot that makes contact with the surface, and the control circuit is configured and arranged with the sensor circuit to manipulate the mechanical actuator to alter the stiffness of the at least one region of the prosthetic foot based on the determined speed.

12. The apparatus of claim 1, wherein
the mechanical actuator is configured and arranged to alter the effective length of the user's leg, with the effective length including the prosthetic foot, and
the control circuit is configured and arranged with the sensor circuit to manipulate the mechanical actuator to alter the effective length of the user's leg based on the sensed movement parameters.

13. The apparatus of claim 1, wherein the control circuit is configured and arranged with the sensor circuit to generate a real-time reconstruction of motion of the prosthetic foot, and to dynamically position the heel region relative to the ball region based on the real-time reconstruction of motion of the prosthetic foot.

14. The apparatus of claim 1, further including the prosthetic foot and a motor, the motor being configured and arranged to move the mechanical actuator to position the prosthetic foot, in response to inputs from the control circuit.

15. The apparatus of claim 1, wherein the control circuit is configured and arranged to predict future movement of the prosthetic foot relative to the surface based on the sensed movement parameters detected over time, and to dynamically position the prosthetic foot based on the predicted future movement of the prosthetic foot.

16. An apparatus comprising:
a mechanical actuator configured and arranged to position a prosthetic foot having a front ball region and a rear heel region for respectively contacting a surface along which a user of the prosthetic foot is travelling;
a sensor circuit configured and arranged to sense movement parameters pertaining to movement of the user; and
a control circuit configured and arranged with the sensor circuit to
determine a state of movement of the user, including a speed at which the user is travelling along the surface, based on the movement parameters sensed by the sensor circuit, and
dynamically position the prosthetic foot while the user is moving in response to the speed at which the user is travelling along the surface by manipulating the mechanical actuator to move the rear heel region relative to the front ball region based on changes in the speed and to gradually eliminate the heel region from contributing to contact between the prosthetic foot and ground as the speed increases.

17. An apparatus comprising:
a mechanical actuator configured and arranged to position a prosthetic foot having a front ball region and a rear heel region for respectively contacting a surface along which a user of the prosthetic foot is travelling; and
a control circuit configured and arranged with the mechanical actuator to determine a state of movement of the user, including a speed at which the user is travelling along the surface, and to cause the mechanical actuator to move the rear heel region relative to the front ball region based on changes in the speed, by at least one of:
increasing or decreasing the height of the rear heel region relative to the front ball region, and
moving the rear heel region toward or away from the front ball region.

18. A method comprising:
sensing movement parameters pertaining to movement of a user of a prosthetic foot as the user travels along a surface, the prosthetic foot having a front ball region and a rear heel region for respectively contacting the surface; and
determining a state of movement of the user, including a speed at which the user is travelling along the surface, based on the sensed movement parameters, and
utilizing a mechanical actuator, dynamically positioning the prosthetic foot in response to the speed at which the user is travelling along the surface, by manipulating the mechanical actuator to move the rear heel region relative to the front ball region based on changes in the speed.

19. The method of claim 18, wherein manipulating the mechanical actuator to move the rear heel region relative to the front ball region based on changes in the speed includes at least one of:
increasing or decreasing the height of the rear heel region relative to the front ball region; and
moving the rear heel region toward or away from the front ball region.

20. The method of claim 18,
wherein determining the state of movement of the user includes reconstructing a model of motion of the prosthetic foot and computing the speed at which the user is travelling;
further including generating a map of desired motion of the prosthetic foot, based on the computed speed; and
wherein dynamically positioning the prosthetic foot includes using the generated map of desired motion to determine a position of the prosthetic foot, and manipulating the mechanical actuator to manipulate the prosthetic foot into the determined position.

* * * * *